(12) United States Patent
Sato et al.

(10) Patent No.: US 6,706,916 B1
(45) Date of Patent: Mar. 16, 2004

(54) OPTICALLY ACTIVE AMINO ACID DERIVATIVES AND PROCESSES FOR THE PREPARATION OF THE SAME

(75) Inventors: Haruyo Sato, Nagoya (JP); Takae Ohno, Tokai (JP); Shiho Iwata, Ichinomiya (JP)

(73) Assignee: Toray Fine Chemicals Co., Ltd. (JP)

( * ) Notice: Subject to any disclaimer, the term of this patent is extended or adjusted under 35 U.S.C. 154(b) by 0 days.

(21) Appl. No.: 09/913,822
(22) PCT Filed: Feb. 10, 2000
(86) PCT No.: PCT/JP00/00749
§ 371 (c)(1), (2), (4) Date: Aug. 17, 2001
(87) PCT Pub. No.: WO00/50382
PCT Pub. Date: Aug. 31, 2000

(30) Foreign Application Priority Data

Feb. 23, 1999 (JP) .......................... 11-044340
Mar. 2, 1999 (JP) .......................... 11-054699
May 11, 1999 (JP) .......................... 11-130619

(51) Int. Cl.$^7$ .......................................... C07C 309/00
(52) U.S. Cl. .................. 562/126; 562/533; 562/433; 562/400
(58) Field of Search .............. 562/130, 533, 562/433, 400

(56) References Cited

FOREIGN PATENT DOCUMENTS

| EP | 0 252 744 A2 | 1/1988 |
| JP | 1-110651 A | 4/1989 |

OTHER PUBLICATIONS

Schuetzner et al, Journal of Chromathography A, vol. 719, pp 411–420, 1996.*

Akimova et al, Vstik Moskovskogo Universiteta, No. 1, 1965, pp 65–68.*

Schuetzner, Wolfgang, et al., "Separation of disastereomers by capillary zone elecrophoresis in free solution with polymer additive and organic solvent component. Effect of pH and solvent composition", J. Chromatogr., A, 1996, vol. 719, No. 2, p. 411–420.

Chem. Abstr., vol. 63, 1965, Col. 3032, The abstract No. 3032f, Akimova, L.N., et al.,'use of a double (N–benzyl-carbobenzoxy)–protection in a synthesis of optically–active peptides', Vestn. Mosk. Univ., Ser. II, Khim., vol. 20, No. 1, 1965, p. 65–68.

Wolfgang Schützner et al., "Separation of diastereomers by capillary zone electrophoresis in free solution with polymer additive and organic Solvent component. Effect of pH and solvent composition", 1996, Journal of Chromatography A, 719, pp. 411–420.

W. Lindner and et al., "Liquid Chromatographic Separation of Enantiomeric Alkanolamines Via Diastereomeric Tartaric Acid Monoesters", 1984, Journal of Chromatography, 316, pp. 605–616.

Madhup K. Dhaon et al., Esterification of N–Protected α–Amino Acids with Alcohol/Carbodiimide/4–(Dimethylamino)–pyridine. Racemization of Aspartic and Glutamic Acid Derivatives, 1982, 47, pp. 1962–1965.

Leonidas Zervas et al., "Studies of Arginine Peptides. I. Intermediates in the Synthesis of N–Terminal and C–Terminal Arginine Peptides", 1957, pp. 1515–1521.

* cited by examiner

Primary Examiner—Alan L. Rotman
Assistant Examiner—Hector M Reyes
(74) Attorney, Agent, or Firm—Piper Rudnick LLP

(57) ABSTRACT

In producing optically-active amino acid benzyl esters by reacting optically-active amino acids with benzyl alcohols, hydrazines are present in the reaction system, or the compounds are reacted in the absence of oxygen, or the compounds are reacted in the absence of oxygen while hydrazines are present in the reaction system. The processes are simple and give optically-active amino acid benzyl esters of high optical purity.

13 Claims, 4 Drawing Sheets

| Time | Area | Area % |
|---|---|---|
| 39.772 | 6962931 | 46.47 D-L |
| 42.411 | 8019317 | 53.53 D-D |
| Total | 14982248 | 100.00 |

OPTICALLY ACTIVE AMINO ACID DERIVATIVES AND PROCESSES FOR THE PREPARATION OF THE SAME

TECHNICAL FILED

The present invention relates to a process for preparing optically-active amino acid (di)benzyl esters, to a process for preparing optically-active amino acid (di)benzyl ester sulfonates, and to optically-active amino acid (di)ester tartramic acids and a process for preparing them.

Optically-active amino acid benzyl esters, optically-active amino acid dibenzyl esters and their sulfonates are useful for materials for medicines and agricultural chemicals, and the present invention relates to processes for preparing amino acid benzyl esters and amino acid dibenzyl esters of high optical purity through simple operations not lowering the optical purity of the optically-active amino acids. Notonly optically-active α-amino acid ester tartramic acids and optically-active α-amino acid diester tartramic acids are useful for materials for medicines and agricultural chemicals, but also they are easy to optically resolve as having a plurality of asymmetric carbon atoms, and, in addition, their optical purity can be accurately determined through HPLC analysis with ordinary reversed-phase columns.

BACKGROUND ART

A method of producing optically-active amino acid benzyl esters by reacting an optically-active amino acid with excessive benzyl alcohol in benzene in the presence of paratoluenesulfonic acid monohydrate therein in a mode of continuous azeotropic dehydration (Dean-Stark reaction) is known from long ago. (Journal of Organic Chemistry, Vol. 22, page 1515 (1957).) For thermally unstable amino acids, also known is a method of producing optically-active amino acid benzyl esters, which comprises adding benzyl alcohol and dimethylaminopyridine to an optically-active amino acid of which the amino group is protected with a tertiary butoxycarbonyl group (Boc group) or the like, dehydrating it with 1-ethyl-3-(3-dimethylaminopropyl)carbodiimide with stirring in a solvent of dichloromethane at 0° C. to thereby prepare an N-protected amino acid benzyl ester, and thereafter removing the protective group from it. (Journal of Organic Chemistry, Vol. 47, page 1962 (1982).) On the other hand, optically-active α-amino acid ester tartramic acids, and optically-active α-amino acid diester tartramic acids are novel compounds, and no one knows how to produce them.

However, the method of continuous azeotropic dehydration (Dean-Stark reaction) of reacting an optically-active amino acid with excessive benzyl alcohol in benzene in the presence of paratoluenesulfonic acid monohydrate therein is accompanied by racemization. Especially for amino acids that require high temperature and take long time for esterification, benzyl esters of high optical purity are difficult to obtain from them. The method of first esterifying an optically-active amino acid of which the amino group has been protected, with benzyl alcohol and then removing the protective group from the resulting ester is not accompanied by racemization as the condition for esterification therein is mild, but it requires complicated operations. Therefore, the method is problematic, if used for producing amino acid benzyl esters and amino acid dibenzyl esters of high optical purity on an industrial scale.

The problem with the present invention is how to produce amino acid benzyl esters and amino acid dibenzyl esters of high optical purity through simple operations on an industrial scale, not lowering the optical purity of optically-active amino acids used as starting materials. Optically-active amino acid ester tartramic acids and optically-active amino acid diester tartramic acids are novel substances.

DISCLOSURE OF THE INVENTION

In producing optically-active amino acid benzyl esters or optically-active amino acid dibenzyl esters by reacting an optically-active amino acid with a benzyl alcohol in the presence of an acid catalyst, when a hydrazine is present in the reaction system, or when the reaction is effected in the absence of oxygen, or when a hydrazine is present in the reaction system and the reaction is effected in the absence of oxygen, then optically-active amino acid benzyl esters or dibenzyl esters of high optical purity can be obtained.

In addition, when an optically-active diacyltartaric anhydride is reacted with an optically-active amino acid ester or diester, or is reacted with a racemic amino acid ester or diester and then optically resolved, then optically-active amino acid ester tartramic acids or optically-active amino acid diester tartramic acids can be produced.

BEST MODES OF CARRYING OUT THE INVENTION

Figure 1:
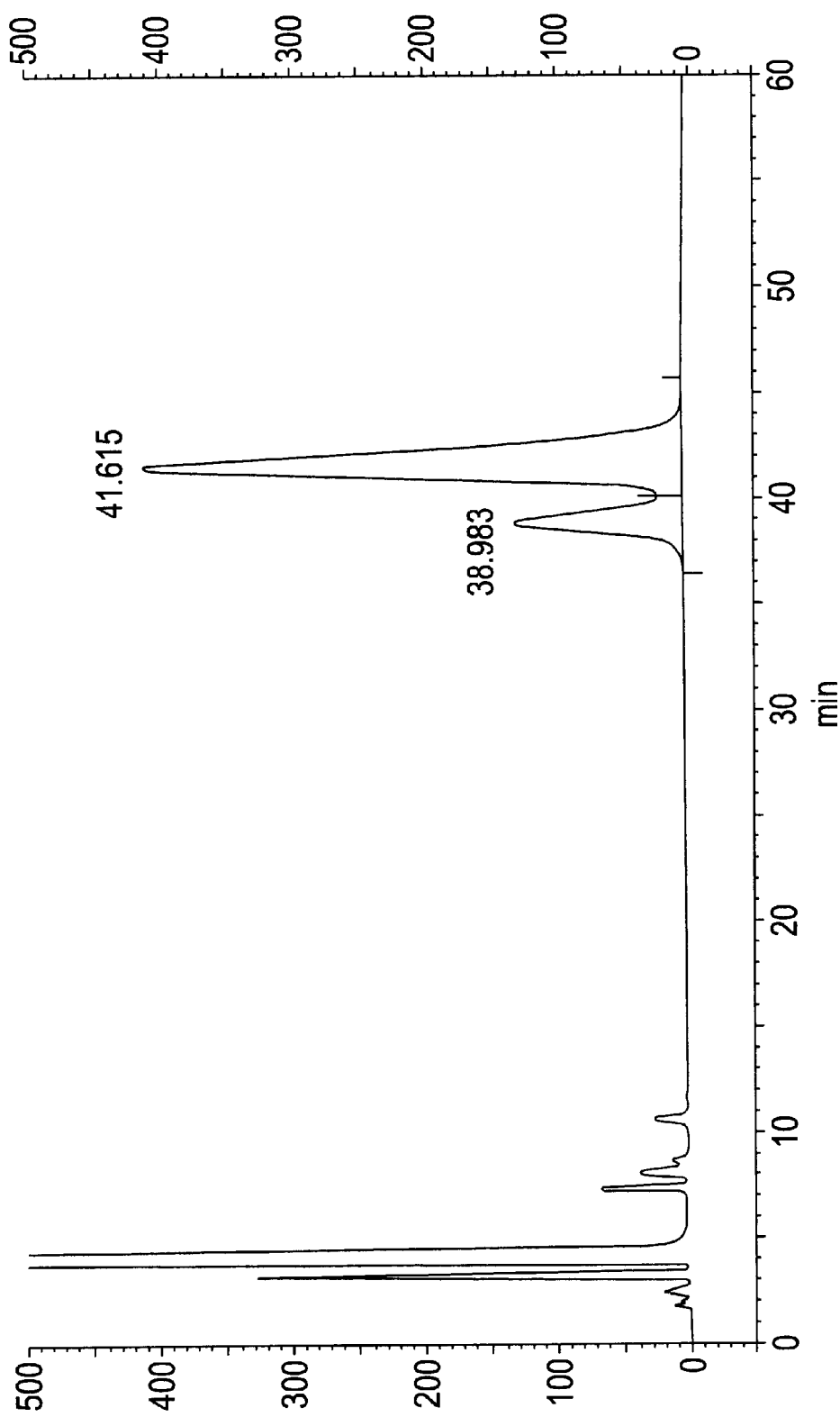
FIG. 1 is a graph showing the HPLC peaks of a mixture of O,O'-diparatoluoyl-L-tartaric acid mono-L-(1,2-dibenzyloxycarbonyl)ethylamide and O,O'-diparatoluoyl-L-tartaric acid mono-D-(1,2-dibenzyloxycarbonyl)ethylamide in Example 11.

Amino acids for starting materials of the invention are optically-active neutral amino acids or optically-active basic amino acids of a general formula (1), or optically-active acidic amino acids of a general formula (2).

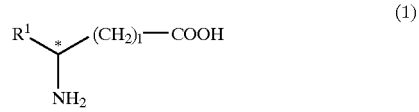
(1)

wherein $R^1$ represents a lower alkyl group, an alkoxyalkyl group, a hydroxyalkyl group, a cycloalkyl group, an aminoalkyl group, a carbamoylalkyl group, an aryl group of which the aromatic ring is unsubstituted or substituted, an arylalkyl group of which the aromatic ring is unsubstituted or substituted, or an indolymethyl group; 1 means an integer of from 0 to 2; and * indicates that the compounds are optically active.

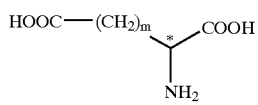

(2)

wherein m means an integer of from 1 to 4; and * has the same meaning as above.

The optically-active amino acids are meant to indicate amino acids of which the amino group is bonded to the asymmetric carbon atom therein, and these includes not only naturally-existing amino acids but also any and every amino acid produced through chemical synthesis. Concretely, they include alanine, valine, glutamine, phenylglycine, phenylalanine, tryptophan, tyrosine, 2-naphthylalanine, etc.; β-amino acids such as 3-aminobutyric acid, etc.; basic α-amino acids such as lysine, ornithine, etc.; and acidic α-amino acids such as aspartic acid, glutamic acid, etc.

The amino acids to be subjected to benzyl-esterification herein are any of L- or D-optically-active amino acids.

For starting materials to be reacted with optically-active diacyltartaric anhydrides to directly obtain optically-active amino acid ester tartramic acids or optically-active amino acid diester tartramic acids, herein used are any of such L- or D-optically-active amino acids. On the other hand, for those to be reacted with optically-active diacyltartaric anhydrides and then optically resolved, usable are racemic amino acid esters of a general formula (14) and racemic amino acid diesters of a general formula (15).

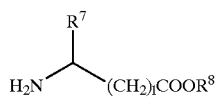

(14)

wherein $R^7$, $R^8$ and 1 have the same meanings as above.

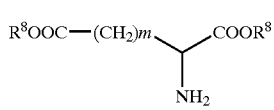

(15)

wherein $R^8$ and m have the same meanings as above.

The racemic compounds are meant to indicate mixtures of L- and D-compounds in any ratio. The optically-active compounds are meant to indicate that either one of L- or D-compound accounts for at least 99%.

Benzyl alcohols serving as the starting materials for benzyl-esterification may be any ones not containing oxidation products, for example, including those of a general formula (3) in which the aromatic ring may be substituted.

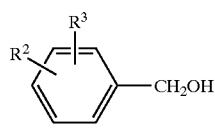

(3)

wherein $R^2$ and $R^3$ each represent a hydrogen atom, a lower alkyl group, a lower alkoxyl group, or a halogen atom, and they may be the same or different.

Concretely, they include benzyl alcohols substituted with lower alkyl group(s), such as 4-methylbenzyl alcohol, 2,4-dimethylbenzyl alcohol, etc.; benzyl alcohols substituted with lower alkoxyl group(s), such as 4-methoxybenzyl alcohol, etc.; and benzyl alcohols substituted with halogen (s), such as 3-chlorobenzyl alcohol, etc.

Preferably, benzyl alcohols are used herein after purified through distillation. In particular, when they contain oxidation products, it is desirable that are purified in pre-treatment and then used herein. For pre-treating them, benzyl alcohols are diluted with toluene, then a small amount of 2,4-dinitrophenylhydrazine is added thereto and stirred at 80° C. for 2 hours, and purified through distillation. If benzyl alcohols containing oxidation products are used, they will cause racemization even under the reaction condition with no oxygen, and are therefore unfavorable. In addition, when hydrazines are to be added to the reaction system, their amount must be increased.

The amount of the benzyl alcohols to be used preferably falls between 1.0 and 10.0 molar times, more preferably between 1.1 and 5.0 molar times the carboxyl group of the amino acid to be reacted therewith. Within the range, the reaction is good with no problem.

In the invention, an acid is present in the reaction system, serving as an esterification catalyst. For the acid catalyst, usable are mineral acids such as sulfuric acid, hydrochloric acid, etc.; and organic sulfonic acids such as paratoluenesulfonic acid, etc. Preferred is paratoluenesulfonic acid. Paratoluenesulfonic acid may be any of easily-available monohydrate or non-hydrate thereof. Its amount to be used must be equivalent to the amino group to be neutralized therewith and must be a catalytic amount enough for esterification. The catalytic amount for esterification preferably falls between 0.01 and 0.30 equivalents, more preferably between 0.05 and 0.20 equivalents to the carboxyl group to be esterified therewith. Concretely, for alanine, the amount of the acid to be used preferably falls between 1.01 and 1.30 times by mol (of alanine); for glutamic acid, between 1.02 and 1.60 times by mol (of glutamic acid); and for lysine, between 2.01 and 2.30 times by mol (of lysine). In case where paratoluenesulfonic acid monohydrate is used, it may be directly used as it is. If desired, however, an amino acid and paratoluenesulfonic acid monohydrate may be mixed in an organic solvent capable of forming an azeotrope with water, then the mixture is subjected to azeotropic dehydration to thereby previously remove the monohydrate water, and thereafter they may be reacted with benzyl alcohols added thereto.

An organic solvent may be or may not be added to the reaction system, but is preferably added thereto for reducing the amount of benzyl alcohols to be used. If water formed in esterification is removed out of the system through distillation, it promotes the esterification speed and increases the esterification yield. In particular, for continuous azeotropic dehydration of Dean-Stark reaction, preferably used are benzene, toluene and xylene capable of forming a great azeotrope with water and capable of well dissolving the starting materials and the products. Especially preferred is toluene. Though depending on the type of the amino acids used and the amount of the benzyl alcohols to be reacted therewith, the amount of the solvent to be used may generally falls between 0.5 and 10.0 times by weight, but preferably between 2.0 and 8.0 times by weight of the benzyl alcohols used. Within the range, the production efficiency is good with no problem.

The hydrazines serving as a racemization inhibitor may be any of aliphatic hydrazines or aromatic hydrazines, but preferred are aromatic hydrazines in view of the solubility thereof in the reaction solvent. Especially preferred are aromatic hydrazines of a general formula (6).

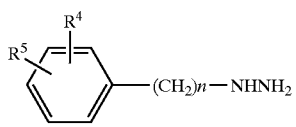

(6)

wherein $R^4$ and $R^5$ each represent a hydrogen atom, a lower alkyl group, a halogen atom, or a nitro group, and they may be the same or different; and n indicates an integer of from 0 to 3.

The lower alkyl group for $R^4$ and $R^5$ preferably has from 1 to 6 carbon atoms. Especially preferred substituents in the hydrazines are a hydrogen atom, a methyl group, an ethyl group, a chlorine atom, and a nitro group. Concretely, phenylhydrazine, 4-chlorophenylhydrazine, 2,4-dinitrophenylhydrazine and benzylhydrazine are preferably used. More preferred are phenylhydrazine and benzylhydrazine. With them, the optically-active amino acid benzyl esters and the optically-active amino acid dibenzyl esters produced are easy to purify. Though depending on the esterification condition and the amount of the benzyl alcohols used, the amount of the hydrazines to be used preferably falls between 0.0005 and 0.050 times by mol, more preferably between 0.0008 and 0.010 times by mol of the benzyl alcohols. Regarding the mode of their addition, the hydrazines maybe added to the reaction system before the start of the reaction, or may be added thereto along with benzyl alcohols.

In case where the reaction is effected in the absence of oxygen to prevent racemization, the starting amino acid is first mixed with an acid and optionally with an organic solvent and then the reaction system is well purged with an inert gas such as nitrogen, helium, argon or the like, or after the reaction system has been degassed into vacuum to completely remove the dissolved oxygen and its pressure is controlled to a desired level with an inert gas such as nitrogen, helium, argon or the like introduced thereinto, and thereafter a benzyl alcohol is added to and reacted with the amino acid. The absence of oxygen in the reaction system means that the oxygen concentration in the vapor phase of the reaction system is preferably at most 1%, more preferably at most 3000 ppm. Though depending on the type of the amino acids and the benzyl alcohols used, the oxygen concentration below the defined level will be good enough to prevent racemization in esterification at 90° C. for 10 hours.

If the esterification is effected in the presence of hydrazines added to the reaction system and in the absence of oxygen in the system, it inhibits racemization more effectively. In particular, the esterification in the absence of oxygen is preferred as the amount of the hydrazines to be added can be reduced and the products are easy to purify.

The reaction temperature shall vary, depending on the type of the optically-active amino acids and the amount of the benzyl alcohols used and also on the reaction pressure, but preferably falls between 60 and 180° C., more preferably between 80 and 130° C. Within the temperature range, the amount of the by-products that may be formed will be small, and the esterification goes on well. The reaction time varies, depending on the reaction temperature, the type of the amino acids and the amount of the benzyl alcohols used, but may generally falls between 3 and 15 hours.

The reaction pressure may be any of atmospheric pressure, reduced pressure or increased pressure.

After the esterification, the products are isolated in any ordinary manner. For example, the reaction liquid is cooled, and the crystals deposited therein may be filtered.

The optically-active amino acid benzyl esters thus isolated are represented by a general formula (4); and the optically-active amino acid dibenzyl esters are represented by a general formula (5).

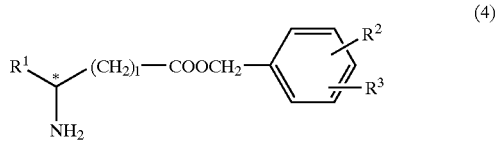

(4)

wherein $R^1$, $R^2$, $R^3$, 1 and * have the same meanings as above.

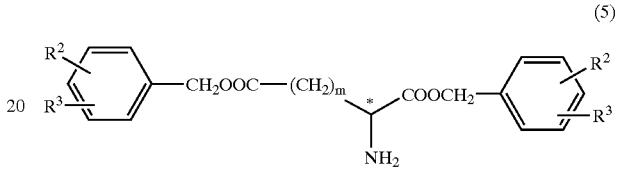

(5)

wherein $R^2$, $R^3$, * and m have the same meanings as above.

These compounds are in the form of their salts with the acid used in the reaction, and, for example, they are in the form of paratoluenesulfonates. For obtaining optically-active amino acid benzyl esters and optically-active amino acid dibenzyl esters of free forms, their salts produced in the manner as above are brought into contact with an aqueous solution of sodium hydroxide or sodium hydrogencarbonate, and then extracted with toluene or the like to thereby isolate their free forms.

The thus-isolated amino acid benzyl esters and amino acid dibenzyl esters contain the non-reacted amino acids and the acid used for the catalyst and even reaction by-products, and their chemical purity is not so high. In particular, when organic sulfonic acids are used, excessive organic sulfonic acids will be in the precipitated crystals to lower the chemical purity of the crystals.

Next described is a process for obtaining amino acid benzyl ester sulfonates and amino acid dibenzyl ester sulfonates of high chemical purity.

Amino acid benzyl ester sulfonates may be represented by a general formula (7); and amino acid dibenzyl ester sulfonates may be represented by a general formula (8).

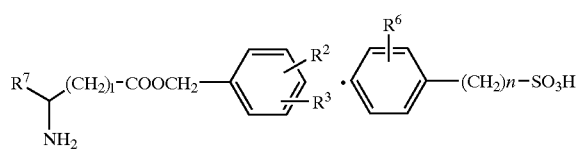

(7)

wherein $R^7$ represents a lower alkyl group, an alkoxyalkyl group, a hydroxyalkyl group, a cycloalkyl group, a carbamoylalkyl group, an aryl group of which the aromatic ring is unsubstituted or substituted, or an arylalkyl group of which the aromatic ring is unsubstituted or substituted; $R^2$, $R^3$ and 1 have the same meanings as above; $R^6$ represents a hydrogen atom, or a lower alkyl group having from 1 to 3 carbon atoms, and it is positioned in any of ortho-, meta- or para-position; n falls between 0 and 3; and * indicates that the compounds are optically active.

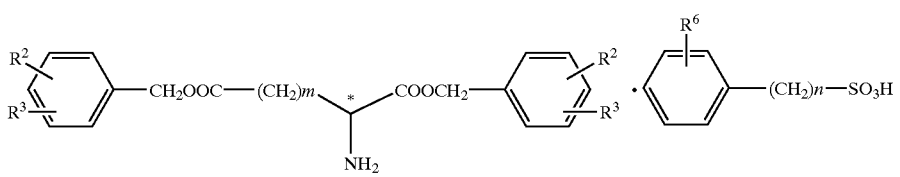

(8)

wherein $R^2$, $R^3$, $R^6$, m and n have the same meanings as above.

The starting amino acid benzyl ester sulfonates and amino acid dibenzyl ester sulfonates for use herein may be produced in any process. For example, L-aspartic acid, paratoluenesulfonic acid and benzyl alcohol are dissolved under heat at 110 to 120° C., then benzene is added thereto, and the L-aspartic acid is benzyl-esterified through azeotropic dehydration. Next, benzene is removed by concentrating the reaction mixture, then diethyl ether and petroleum ether are added to system, and the crystals thus precipitated are taken out through filtration. The thus-obtained, crude dibenzyl aspartate sulfonate can be used as the starting compound in the invention. Its L-form and D-form or their mixture can also be used.

The crude crystals contain the non-reacted amino acid, the excessive sulfonic acid, amino acid-derived reaction by-products, benzyl alcohol-derived reaction by-products, etc. For purifying the crude amino acid benzyl ester sulfonates and amino acid dibenzyl ester sulfonates that contain such water-soluble impurities and oil-soluble impurities, they may be recrystallized from an organic solvent. In general, however, amino acid ester sulfonates are slightly soluble in organic solvents except alcohols. Therefore, for completely dissolving them, a large amount of solvent is needed, and, in addition, sulfonic acid- and amino acid-derived impurities that are slightly soluble in organic solvents could not be effectively removed. On the other hand, in case where the crude products are recrystallized from water, a large amount of water is needed for completely dissolving them if they contain slightly-soluble impurities, and, in addition, high-temperature recrystallization is unfavorable as causing hydrolysis of the ester group in the products. Moreover, in the method, benzyl alcohols and benzyl alcohol-derived oil-soluble impurities cannot be removed.

For effectively purifying amino acid benzyl ester sulfonates and amino acid dibenzyl ester sulfonates that contain a relatively small amount of water-soluble impurities, the following method is employable. Concretely, the crude crystals are suspended in an organic solvent, then, while they are stirred at a predetermined temperature, water of which the amount is at least 2 times by mol of the crude starting amino acid is added thereto to completely dissolve them, and thereafter the resulting solution is cooled to precipitate crystals. The thus-precipitated crystals are taken out through filtration, and dried.

It is desirable that the organic solvent to be used in the method does not react with amino acid benzyl ester sulfonates and amino acid dibenzyl ester sulfonates and that its solubility is at most 5 g/100 g at 20° C. Preferably, the organic solvent is at least one selected from aromatic hydrocarbons, aliphatic hydrocarbons, ethers, halides, nitrites and ketones, more preferably, any of acetonitrile, tetrahydrofuran, benzene, toluene, xylene, etc.

The temperature for dissolution may fall between 30° C. and the boiling point of the solvent used, but it is desirable that the difference between the dissolution temperature and the crystallization temperature is large for better purification efficiency.

On the other hand, for purifying crude amino acid benzyl ester sulfonates and crude amino acid dibenzyl ester sulfonates that contain a relatively large amount of water-soluble impurities, the following method is effective. Concretely, the crude crystals are suspended in an organic solvent, then, while they are stirred at a predetermined temperature, water of which the amount is at least 2 times by mol, preferably from 10 to 20 times by mol of the starting amino acid is added thereto to completely dissolve them, and thereafter the resulting solution is statically kept as it is, and the separated aqueous layer is removed. Next, the amino acid benzyl ester sulfonates and the amino acid dibenzyl ester sulfonates in the organic layer are cooled and crystallized, and the thus-precipitated crystals are taken out through filtration.

It is desirable that the organic solvent to be used in the method does not react with amino acid benzyl ester sulfonates and amino acid dibenzyl ester sulfonates, that its solubility is at most 5 g/100 g at room temperature, and that it can be separated from water through liquid-liquid separation. Preferably, the organic solvent is at least one selected from aromatic hydrocarbons, aliphatic hydrocarbons, ethers, halides, nitriles and ketones, more preferably, any of benzene, toluene, xylene, etc. The temperature for dissolution may fall between 30° C. and the boiling point of the solvent used, but it is desirable that the difference between the dissolution temperature and the crystallization temperature is large for better purification efficiency.

In case where water-soluble impurities still remain in the thus-isolated amino acid benzyl ester sulfonates and amino acid dibenzyl ester sulfonates, the isolated crystals shall be repeated washed with water. For isolating the amino acid benzyl ester sulfonates and amino acid dibenzyl ester sulfonates from the organic solvent, the organic layer containing them may be directly cooled and precipitated, and the thus-precipitated crystals may be taken out through filtration and dried.

For effectively carrying out the purification method, it may be effected in a mode of continuous purification. For example, aspartic acid and benzyl alcohol are suspended in a solvent of benzene, then they are reacted through Dean-Stark dehydration in the presence of paratoluenesulfonic acid serving as a catalyst to form dibenzyl aspartate, and thereafter water is added thereto at 60 to 70° C. to wash away the water-soluble impurities such as the non-reacted aspartic acid, the reaction intermediate monobenzyl aspartate, the excess toluenesulfonic acid, etc. Next, the benzene layer is dewatered through Dean-Stark azeotropic dehydration, and thereafter cooled and precipitated. In that manner, obtained is dibenzyl aspartate sulfonate of high purity.

The optical purity of the amino acid benzyl ester sulfonates and the amino acid dibenzyl ester sulfonates purified in the manner as above does not substantially lower after the purification treatment.

Next described is the reaction of optically-active diacyl-tartaric anhydrides with amino acid esters or amino acid diesters.

The amino acid esters used as the starting material in the invention are amino acid esters of a general formula (11) or amino acid diesters of a general formula (12).

(11)

wherein $R^7$, $R^8$, l and * have the same meanings as above.

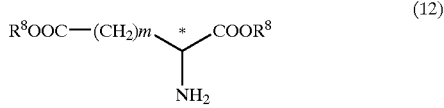

(12)

wherein $R^8$, m and * have the same meanings as above.

For chemically stably storing them, in general, amino acid esters and amino acid diesters are mostly in the form of their acid-addition salts. For the starting materials in the invention, however, they may be in any form of free esters or their acid-addition salts. The acid-addition salts may be inorganic acid salts with hydrochloric acid, sulfuric acid or the like; or organic sulfonic acid salts with benzenesulfonic acid, toluenesulfonic acid or the like; or organic carboxylic acid salts with acetic acid, propionic acid or the like. Optically-active L- or D-forms of the compounds may also be used. In case where the products are optically resolved, the starting materials for them may be mixtures of L- and D-form compounds.

In formulae (11) and (12), the ester group may be any of aliphatic esters with lower alcohols, or aromatic esters with benzyl alcohols, etc. In the aromatic esters, the aromatic ring may be substituted. For example, usable are esters of lower alkyl-substituted benzyl alcohols such as 4-methylbenzyl alcohol, 2,4-dimethylbenzyl alcohol, etc.; those of lower alkoxy-substituted benzyl alcohols such as 4-methoxybenzyl alcohol, etc.; those of halogen-substituted benzyl alcohols such as 3-chlorobenzyl alcohol, etc.; and those of phenylethyl alcohols.

The optically-active diacyltartaric anhydrides of the other starting material are compounds of a general formula (13) in which the two hydroxyl groups of the tartaric acid are esterified with an aromatic carboxylic acid.

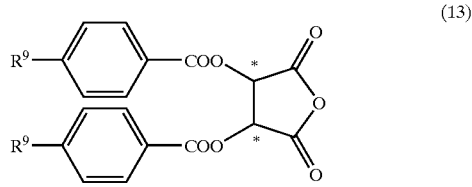

(13)

wherein $R^9$ and * have the same meanings as above.

The aromatic carboxylic acid to form the esters includes aromatic carboxylic acids such as benzoic acid, paratoluic acid, 2,4-dimethylbenzoic acid, 4-methoxybenzoic acid, 4-chlorobenzoic acid, etc.; and aralkylcarboxylic acids such as phenylacetic acid, etc. Preferred are esters of benzoic acid, paratoluic acid or 4-methoxybenzoic acid. Optically-active diacyltartaric acid derivatives of any of L- or D-form may be used herein, but their optical purity must be at least 99.5% ee.

Regarding the mode of their reaction, the amino acid ester or amino acid diester is reacted with the optically-active diacyltartaric anhydrides in a solvent. In case where the amino acid ester or the amino acid diester to be the starting material is in the form of an acid-addition salt, the salt is previously neutralized with an alkali metal hydroxide such as sodium hydroxide, potassium hydroxide or the like or with an alkali metal carbonate such as sodium hydrogencarbonate, sodium carbonate or the like, and its free ester or diester is used herein.

The reaction solvent may be any and every one that does not interfere with the reaction. For example, usable are hydrocarbons such as toluene, etc.; nitrites such as acetonitrile, etc.; ethers such as diethyl ether, tetrahydrofuran, etc.; halogenohydrocarbons such as dichloromethane, chloroform, etc. Their mixtures may also be used, and they may contain water with no problem. However, if too much base is used for neutralizing their acid-addition salts, the excess base still remaining in the neutralized amino acid esters will hydrolyze the esters and the optically-active diacyltartaric anhydrides. Therefore, it is desirable that the base to be used for neutralization is an equivalent amount to the neutralization.

The reaction temperature preferably falls between 0° C. and 100° C., more preferably between room temperature and 40° C. The reaction time depends on the reaction temperature and the amount of the optically-active diacyltartaric anhydride used. In general, however, the reaction will finish in 0.1 to 5.0 hours. Under the condition, the optical purity of the optically-active diacyltartaric acid derivative does not lower. In addition, the optical purity of the other starting material, amino acid ester does not also lower.

The amount of the optically-active diacyltartaric anhydride to be used may well be at least the equimolar amount to the amino acid ester or amino acid diester to be reacted with the anhydride, but is preferably at least two times by mol of the anhydride. Within the range, the conversion rate of the amino acid ester or the amino acid diester is kept nearly constant.

After the reaction, the products are isolated in an ordinary manner. However, depending on the type of the amino acid ester or the amino acid diester used and on the type of the optically-active diacyltartaric anhydride reacted therewith, different methods of isolation shall be employed. For example, in case where dibenzyl aspartate is reacted with dibenzoyl L-tartaric anhydride in chloroform, the reaction mixture is washed with an aqueous acid solution of, for example, hydrochloric acid to remove the non-reacted dibenzyl aspartate, and thereafter the chloroform layer is concentrated and precipitated to isolate the product, dibenzyl aspartate tartramic acid. In case where the starting amino acid ester or amino acid diester is an optically-active one, the optical purity of the product, amino acid ester tartramic acid or amino acid diester tartramic acid is comparable to the optical purity of the starting ester or diester.

In case where a mixture of L- and D-form compounds is used as the starting material, the product, amino acid ester tartramic acid or amino acid diester tartramic acid is optically resolved.

For optically resolving the product, any ordinary method is employable. For example, the product is resolved through a column, or is recrystallized.

EXAMPLES

The invention is described in detail in the following Examples, to which, however, the invention is not limited.

The racemization rate is obtained through HPLC for optical purity analysis, according to the following equation.

Racemization Rate $(\%)=(X-Y)/X \times 100$ in which
X indicates the optical purity (% ee) of the optically-active amino acid before reaction;
Y indicates the optical purity (% ee) of the amino acid ester produced after reaction.

The optically-active amino acids used in the following Examples are first-class grade chemicals, or are synthesized in situ and optically resolved. Theoheer chemicals are commercially-available, first-class grade chemicals.

EXAMPLE 1

8.9 g (0.1 mols) of L-alanine (99.5% ee), 54.0 g (0.50 mols) of pure benzyl alcohol, 22.8 g (0.12 mols) of paratoluenesulfonic acidmonohydrate, and 50 ml of toluene were fed into a 500-ml Dean-Stark azeotropic dehydration device, and degassed into vacuum with stirring, and then the inner pressure was controlled to be comparable to atmospheric pressure with argon introduced thereinto. In the argon atmosphere under atmospheric pressure, this was heated under reflux for 5 hours, and the water formed was removed through azeotropic dehydration. The amount of the water removed was about 3.5 g. Next, toluene was evaporated away, then the system was cooled to room temperature, and 300 ml of diethyl ether was added thereto and stirred for 2 hours. The precipitated crystals were taken out through filtration and dried to obtain 33.0 g of L-alanine benzyl ester paratoluenesulfonate. This was recrystallized from a mixture of 100 ml of ethanol and 100 ml of diethyl ether. The yield of the thus-obtained L-alanine benzyl ester paratoluenesulfonate was 29.9 g, and 85.2%. The chemical purity of the product was 99.2%, and the optical purity thereof was 99.5% ee. No racemization occurred in the reaction.

EXAMPLE 2

8.9 g (0.1 mols) of L-alanine (99.5% ee), 54.0 g (0.50 mols) of pure benzyl alcohol, 22.8 g (0.12 mols) of paratoluenesulfonic acid monohydrate, 0.5 g (5 mmols) of phenylhydrazine and 50 ml of toluene were fed into a 500-ml Dean-Stark azeotropic dehydration device, and heated under reflux under atmospheric pressure for 5 hours, and the water formed was removed through azeotropic dehydration. The amount of the water removed was about 3.5 g. The reaction mixture was then processed in the same manner as in Example 1, and 29.5 g of pure L-alanine benzyl ester paratoluenesulfonate was obtained. Its chemical purity was 99.2%, and optical purity was 99.5% ee. No racemization occurred in the reaction.

Comparative Example 1

8.9 g (0.1 mols) of L-alanine (99.5% ee) 54.0 g (0.50 mols) of pure benzyl alcohol, 22.8 g (0.12 mols) of paratoluenesulfonic acid monohydrate and 50 ml of toluene were fed into a 500-ml Dean-Stark azeotropic dehydration device, and heated under reflux under atmospheric pressure for 5 hours, and the water formed was removed through azeotropic dehydration. The amount of the water removed was about 3.5 g.

The reaction mixture was then processed in the same manner as in Example 1, and 29.5 g of pure L-alanine benzyl ester paratoluenesulfonate was obtained. Its chemical purity was 99.3%, and optical purity was 95.5% ee. This means that the reaction was accompanied by racemization.

EXAMPLE 3

13.3 g (0.1 mols) of L-aspartic acid (99.5% ee), 32.4 g (0.30 mols) of purebenzylalcohol, 22.8g (0.12mols) of paratoluenesulfonic acid monohydrate, 0.5 g (5 mmols) of phenylhydrazine and 250 ml of toluene were fed into a 500-ml Dean-Stark azeotropic dehydration device, and degassed into vacuum with stirring, and then the inner pressure was controlled to be comparable to atmospheric pressure with argon introduced thereinto. In the argon atmosphere under atmospheric pressure, this was heated under reflux for 10 hours, and the water formed was removed through azeotropic dehydration. The amount of the water removed was about 5.1 g. Next, the reaction mixture was cooled to 70° C. with stirring, and then washed twice with 80 g of water. Water having dissolved in the toluene layer was removed through azeotropic distillation, and then the toluene layer was cooled to room temperature with stirring. The crystals thus precipitated were taken out through filtration and dried to obtain 40.3 g of dibenzyl L-aspartate paratoluenesulfonate. Its yield was 83.0%, chemical purity was 99.6%, and optical purity was 99.5% ee. No racemization occurred in the reaction.

Comparative Example 2

13.3 g (0.1 mols) of L-aspartic acid (99.5% ee), 32.4 g (0.30 mols) of pure benzyl alcohol, 22.8 g (0.12 mols) of paratoluenesulfonic acidmonohydrate and 250 ml of toluene were fed into a 500-ml Dean-Stark azeotropic dehydration device, and heated under reflux under atmospheric pressure for 10 hours, and the water formed was removed through azeotropic dehydration. The reaction mixture was then processed in the same manner as in Example 3, and 41.0 g of dibenzyl L-aspartate paratoluenesulfonate was obtained. Its yield was 84.5% and chemical purity was 99.5%, but optical purity was 92.1% ee. This means that the reaction was accompanied by racemization.

EXAMPLE 4

14.6 g (0.1 mols) of D-lysine (99.0% ee), 16.2 g (0.15 mols) of pure benzyl alcohol, 47.5 g (0.25 mols) of paratoluenesulfonic acid monohydrate, 0.4 g (4 mmols) of phenylhydrazine and 250 ml of toluene were fed into a 500-ml Dean-Stark azeotropic dehydration device, and degassed into vacuum with stirring, and then the inner pressure was controlled to be comparable to atmospheric pressure with argon introduced thereinto. The $O_2$ concentration in the vapor phase was about 2000 ppm. In the argon atmosphere under atmospheric pressure, this was heated under reflux for 10 hours, and the water formed was removed through azeotropic dehydration. The amount of the water removed was about 6.0 g. Next, toluene was evaporated away, then the system was cooled to room temperature, and 300 ml of diethyl ether was added thereto and stirred for 2 hours. The precipitated crystals were taken out through filtration and dried to obtain 48.2 g of D-lysine benzyl ester diparatoluenesulfonate. This was recrystallized from a mixture of 200 ml of ethanol and 200 ml of diethyl ether. The yield of the thus-obtained pure D-lysine benzyl ester diparatoluenesulfonate was 41.2 g, and 71.0%. The chemical purity of the product was 99.3%, and the optical purity thereof was 99.0% ee. No racemization occurred in the reaction.

EXAMPLE 5

11.7 g (0.1 mols) of D-valine (99.0% ee), 32.4 g (0.30 mols) of pure benzyl alcohol, 22.8 g (0.12 mols) of paratoluenesulfonic acid monohydrate, 0.4 g (4 mmols) of phenylhydrazine and 200 ml of toluene were fed into a 500-ml Dean-Stark azeotropic dehydration device, and degassed into vacuum with stirring, and then the inner pressure was controlled to be comparable to atmospheric pressure with argon introduced thereinto. In the argon atmosphere under atmospheric pressure, this was heated under reflux for 20 hours, and the water formed was removed through azeotropic dehydration.

The amount of the water removed was about 3.0 g. The reaction mixture was then processed in the same manner as in Example 1, and 25.8 g of pure D-valine benzyl ester paratoluenesulfonate was obtained. Its yield was 68.0%, chemical purity was 99.3%, and optical purity was 99.0% ee. No racemization occurred in the reaction.

Comparative Example 3

11.7 g (0.1 mols) of D-valine (99.0% ee), 32.4 g (0.30 mols) of pure benzyl alcohol, 22.8 g (0.12 mols) of para-toluenesulfonic acidmonohydrate and 200 ml of toluene were fed into a 500-ml Dean-Stark azeotropic dehydration device, and heated under reflux under atmospheric pressure for 20 hours, and the water formed was removed through azeotropic dehydration. The amount of the water removed was about 3.0 g. The reaction mixture was then processed in the same manner as in Example 5, and 26.2 g of pure D-valine benzyl ester paratoluenesulfonate was obtained. Its yield was 69.1% and chemical purity was 99.2%, but optical purity was 83.5% ee. This means that the reaction was accompanied by racemization.

EXAMPLE 6

13.3 g (0.1 mols) of L-aspartic acid (99.5% ee), 43.2 g (0.4 mols) of pure benzyl alcohol, 22.8 g (0. 12 mols) of paratoluenesulfonic acid monohydrate and 300 ml of toluene were fed into a 500-ml Dean-Stark azeotropic dehydration device, and heated under reflux for 10 hours, and the water formed was removed through azeotropic dehydration. The amount of the water removed was about 5.9 g. Next, the reaction mixture was cooled to room temperature with stirring, and then kept stirred further for 2 hours to precipitate crystals. The thus-precipitated crystals were taken out through filtration and dried to obtain 45.2 g of dibenzyl L-aspartate paratoluenesulfonate. (Its yield was 93.2%.) Its chemical purity was 90.3%, and optical purity was 68.3% ee. 30 g (0.062 mols) of the thus-obtained, crude dibenzyl L-aspartate paratoluenesulfonate was mixed with 150 ml of toluene, and stirred at 70° C. However, most of the crystals did not dissolve, and the mixture looked slurry. 2.25 g (0.125 mols) of water was added thereto, and the undissolved crystals completely dissolved therein. This was kept stirred for 1 hour at 700° C., then cooled to room temperature, and then further stirred for 2 hours for recrystallization. The crystals thus precipitated were taken out through filtration to obtain 25.2 g of dibenzyl L-aspartate paratoluenesulfonate. Its chemical purity increased up to 98.2%, and this means that the product was well purified through recrystallization. The optical purity of the purified product was 68.3% ee.

EXAMPLE 7

30 g (0.062 mols) of dibenzy L-aspartate paratoluenesulfonate having a chemical purity of 91.8% and an optical purity of 98.2% ee was suspended in 150 ml of tetrahydrofuran, and stirred under heat at 60° C. However, most of the crystals did not dissolve, and the mixture looked slurry. 2.25 g (0.125 mols) of water was added thereto, and the crystals completely dissolved therein to give a uniform slurry. This was then processed in the same manner as in Example 1. and 22.5 g of dibenzyl L-aspartate paratoluenesulfonate. Its chemical purity increased up to 98.8%, and this means that the salt was well purified through recrystallization. The optical purity of the purified product was 98.2% ee, and did not lower.

EXAMPLE 8

In Example 2, the solvent shown in Table 1 was used for recrystallization in place of tetrahydrofuran, and the product was recrystallized from the solvent after 2.25 g of water was added thereto. The results are given in Table 1.

TABLE 1

| No. | Solvent | Chemical Purity after |
|---|---|---|
| 1 | methyl isobutyl ketone | 99.1% |
| 2 | chlorobenzene | 98.9% |
| 3 | acetonitrile | 99.0% |
| 4 | methyl isopropyl ketone | 99.3% |

EXAMPLE 9

13.3 g (0.1 mols) of D-aspartic acid (99.5% ee), 21.6 g (0.2 mols) of pure benzyl alcohol, 22.8 g (0.12 mols) of paratoluenesulfonic acid monohydrate and 300 ml of toluene were fed into a 500-ml Dean-Stark azeotropic dehydration device, and heated under reflux for 10 hours, and the water formed was removed through azeotropic dehydration. The amount of the water removed was about 5.4 g. Next, the reaction mixture was cooled to room temperature with stirring, and then kept stirred further for 2 hours to precipitate crystals. The thus-precipitated crystals were taken out through filtration and dried to obtain 40.3 g of dibenzyl D-aspartate paratoluenesulfonate. (Its yield was 83.1%.) Its chemical purity was 91.9%, and optical purity was 71.3% ee. 30 g (0.051 mols) of the thus-obtained, crude dibenzyl D-aspartate paratoluenesulfonate was mixed with 150 ml of toluene, and stirred at 70° C. However, most of the crystals did not dissolve, and the mixture looked slurry. 30 g (1.67 mols) of water was added thereto, and this was kept stirred for 1 hour at 70° C. Stirring it was stopped, and this was kept static for liquid-liquid separation. The aqueous layer thus separated was removed. 30 g of water was again added thereto, and washing it was repeated. After having been thus washed, the toluene layer was dewatered through Dean-Stark azeotropic dehydration to have a water content of at most 0.1%. Next, this was cooled to room temperature, and then stirred for 2 hours for recrystallization. The crystals thus precipitated were taken out through filtration, and 25.3 g of dibenzyl D-aspartate paratoluenesulfonate was obtained. Its chemical purity increased up to 99.2 %, and its optical purity was 68.3% ee.

EXAMPLE 10

13.3 g (0.1 mols) of L-aspartic acid (99.5% ee), 28.1 g (0.26 mols) of pure benzyl alcohol, 22.8 g (0.12 mols) of paratoluenesulfonic acid monohydrate, 0.1 g of phenylhydrazine and 300 ml of toluene were fed into a 500-ml Dean-Stark azeotropic dehydration device, and heated under reflux for 10 hours, and the water formed was removed through azeotropic dehydration. Next, the reaction mixture was cooled to 80° C. with stirring, and washed twice with 50 g of water at 80° C. The thus-washed toluene layer was dewatered through azeotropic dehydration to have a water content of at most 0.1%, then cooled to room temperature, and thereafter kept stirred for 2 hours for recrystallization. The crystals thus precipitated were taken out through filtration and dried, and 44.6 g of dibenzyl L-aspartate paratoluenesulfonate was obtained. (Its yield was 92.0%.) Its chemical purity was 99.3%, and optical purity was 99.3% ee.

Comparative Example 4

L-aspartic acid and not D-aspartic acid was reacted in the same manner as in Example 9, and toluene in the reaction system was reduced to about 100 ml through concentration under reduced pressure. Next, this was cooled to room temperature, and the crystals precipitated were taken out through filtration. The crude crystals were dried, then mixed with 2 liters of water, and heated under reflux, and, while hot, the insoluble crystals were removed through filtration. With stirring, the resulting filtrate was cooled to room temperature, and the crystals thus precipitated were taken out through filtration and dried to obtain 22.2 g of dibenzyl L-aspartate paratoluenesulfonate. Its chemical purity was 98.5%, and was high. However, a larger amount of the solvent was needed for purification herein than in the case of purification with an organic solvent combined with water, and therefore the production efficiency was low.

EXAMPLE 11

Process of Preparing Dibenzyl Aspartate Tartramic Acid 13.3 g (0.1 mols) of L-aspartic acid (99.5% ee), 32.4 g (0.30 mols) of pure benzyl alcohol, 22.8 g (0.12 mols) of paratoluenesulfonic acidmonohydrate and 250 ml of toluene were fed into a 500-ml Dean-Stark azeotropic dehydration device, and heated under reflux under atmospheric pressure for 10 hours with stirring, and the water formed was removed through azeotropic dehydration. The amount of the water removed was about 5.1 g. Next, with stirring, this was cooled to 70° C., and then washed twice with 80 g of water. Water having dissolved in the toluene layer was removed through azeotropic distillation. Then, this was cooled to room temperature with stirring. The crystals precipitated were taken out through filtration and dried, and 40.3 g of dibenzyl L-aspartate paratoluenesulfonate was obtained. Its yield was 83.0%, and chemical purity was 99.6%.

19.4 g of the thus-obtained dibenzyl L-aspartate paratoluenesulfonate was suspended in 150 ml of chloroform, to which was added 16 g (0.04 mols) of aqueous 10% sodium hydroxide solution, and stirred at room temperature for 1 hour. Next, the chloroform layer was separated, to which was added 14.7 g (0.04 mols) of O,O'-diparatoluoyl-L-tartaric anhydride, and again stirred at room temperature for 2 hours. The chloroform layer was analyzed through HPLC. Its chart gave two peaks based on O,O'-diparatoluoyl-L-tartaric acid mono-L-(1,2-dibenzyloxycarbonyl)ethylamide (L-L form) of formula (16) and on O,O'-diparatoluoyl-L-tartaric acid mono-D-(1,2-dibenzyloxycarbonyl)ethylamide (L-D form) of formula (17), and the optical purity of the dibenzyl L-aspartate paratoluenesulfonate used in the reaction was found to be 59.0% ee (FIG. 1—column, CAPCELL PAC SG120; eluent, aqueous phosphoric acid solution (pH 2.2)/methanol=38/62 v/v).

After the reaction, the reaction mixture was washed with 50 ml of aqueous 5% hydrochloric acid solution, and then the chloroform layer was concentrated to obtain 27.8 g of O,O'-diparatoluoyl-L-tartaric acid mono(1,2-dibenzyloxycarbonyl)ethylamide. 10 g of the concentrate was developed and partitioned through a column filled with 500 ml of silica gel, using toluene/cyclohexane, and then concentrated. Thus were obtained 7.2 g of O,O'-diparatoluoyl-L-tartaric acid mono-L-(1,2-dibenzyloxycarbonyl)ethylamide and 1.9 g of O,O'-diparatoluoyl-L-tartaric acid mono-D-(1,2-dibenzyloxycarbonyl)ethylamide.

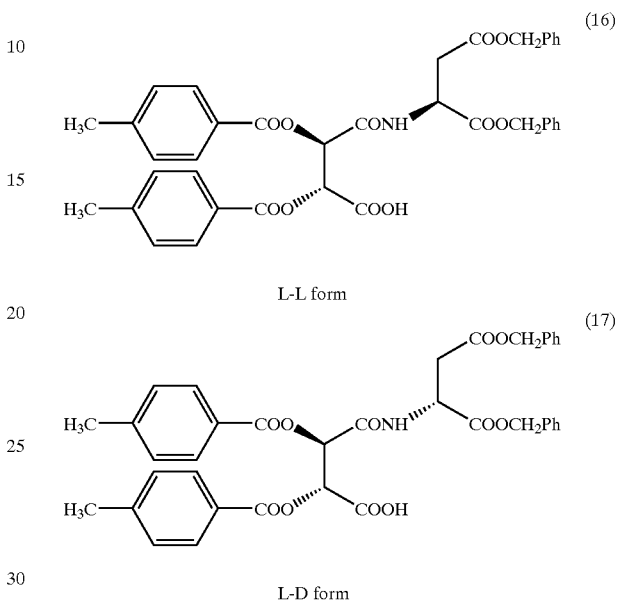

L-L form

L-D form

EXAMPLE 12

Figure 2:
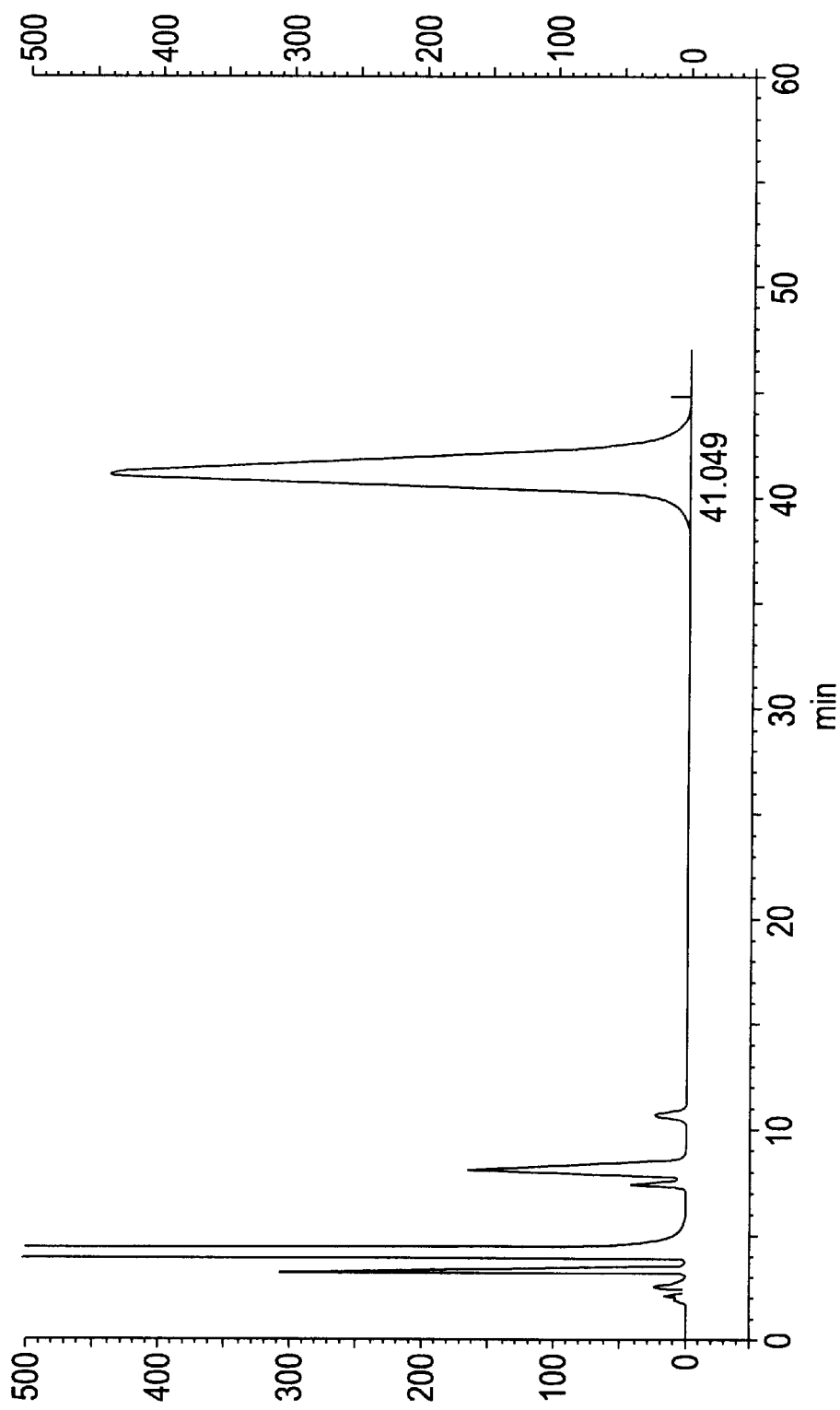
FIG. 2 is a graph showing the HPLC peak of O,O'-diparatoluoyl-L-tartaric acid mono-L-(1,2-dibenzyloxycarbonyl)ethylamide in Example 12.

4.9 g (10 mmols) of dibenzyl D-aspartate paratoluenesulfonate having an optical purity of 99.5% ee was suspended in 50 ml of toluene, to which was dropwise added 10 ml of aqueous 1 N sodium hydroxide solution with stirring at room temperature. This was stirred for 30 minutes, and the aqueous layer was removed through liquid-liquid separation. 3.5 g (9.5 mmols) of O,O'-diparatoluoyl-D-tartaric anhydride was added to the toluene layer, and stirred at room temperature for 1 hour. The reaction mixture was analyzed through HPLC. Its chart gave a single peak for O,O'-diparatoluoyl-D-tartaric acid mono-D-(1,2-dibenzyloxycarbonyl)ethylamide, and this confirms that dibenzyl D-aspartate was not racemized at all in the reaction (FIG. 2—the condition for measurement is the same as that for FIG. 1). Next, 5 ml of 1 N hydrochloric acid was added to the reaction mixture, and stirred at room temperature for 10 minutes to remove the non-reacted dibenzyl D-aspartate. Then, the toluene layer was concentrated to 20 ml, and stirred at 5 to 10° C. for 2 hours. The crystals thus precipitated were taken out through filtration and dried to obtain 5.1 g of O,O'-diparatoluoyl-D-tartaric acid mono-D-(1,2-dibenzyloxycarbonyl)ethylamide. The yield of the thus-isolated product was 75%.

EXAMPLE 13

19.4 g of dibenzyl L-aspartate paratoluenesulfonate prepared in Example 11 was suspended in 150 ml of toluene, to which was added 16 g (0.04 mols) of aqueous 10% sodium hydroxide solution, and stirred at room temperature for 1 hour. Next, the toluene layer was separated, to which was added 14.7 g of O,O'-diparatoluoyl-L-tartaric anhydride, and again stirred at room temperature for 2 hours. The toluene layer was analyzed through HPLC. Its chart gave two peaks, and the optical purity of the dibenzyl L-aspartate paratoluenesulfonate used in the reaction was found to be 59.0% ee.

After the reaction, the reaction mixture was washed with 50 ml of aqueous 5% hydrochloric acid solution, and then the toluene layer was concentrated to 50 ml, and stirred at 5 to 10° C. for 2 hours.

The crystals thus precipitated were taken through filtration and dried to obtain 5.1 g of O,O'-diparatoluoyl-L-tartaric acid mono-L-(1,2-dibenzyloxycarbonyl)ethylamide. Its optical purity was 99.1% ee.

EXAMPLE 14

O,O'-diparatoluoyl-D-tartaric anhydride was reacted with dibenzyl L-aspartate paratoluenesulfonate in the same manner as in Example 12 to obtain O,O'-diparatoluoyl-D-tartaric acid mono-L-(1,2-dibenzyloxycarbonyl)ethylamide of the following formula (18).

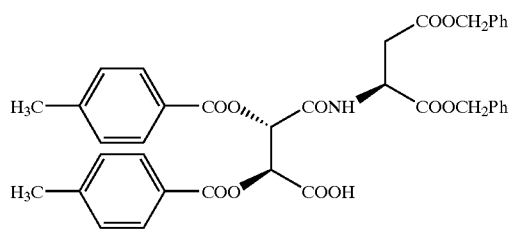

(18)

Its data obtained through analysis are as follows:
m.p.: 52 to 54° C.
$^1$HNMR: 2.2–2.4 ppm(6H), 2.7–3.1 ppm(4H), 4.8–5.0 ppm(4H), 5.0–5.1 ppm(1H), 5.8–6.1 ppm(2H), 7.0–8.0 ppm (20H)
$^{13}$CNMR: 21 ppm, 22 ppm, 36 ppm, 49 ppm, 67 ppm, 68 ppm, 71 ppm, 72 ppm, 125 ppm, 126 ppm, 127–135 ppm, 135 ppm, 144 ppm, 145 ppm, 164.5 ppm 165 ppm, 166 ppm, 170.2 ppm, 170.4 ppm, 170.5 ppm
IR: 3600–2700 cm$^{-1}$, 1800–1650 cm$^{-1}$, 1600 cm$^{-1}$, 1550–1500 cm$^{-1}$, 1450 cm$^{-1}$, 1430 cm$^{-1}$, 1400 cm$^{-1}$, 1350–1150 cm$^{-1}$, 1150–1040 cm$^{-1}$, 1010 cm$^{-1}$, 920 cm$^{-1}$, 850 cm$^{-1}$, 760 cm$^{-1}$, 700 cm$^{-1}$

EXAMPLE 15

O,O'-dibenzoyl-D-tartaric anhydride was reacted with dibenzyl L-aspartate paratoluenesulfonate in the same manner as in Example 12 to obtain O,O'-dibenzoyl-D-tartaric acid mono-L-(1,2-dibenzyloxycarbonyl)ethylamide of the following formula (19).

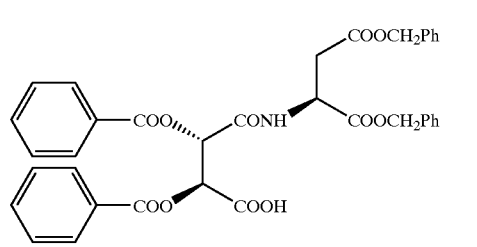

(19)

Its data obtained through analysis are as follows:
m.p.: 49 to 51° C.
$^1$HNMR: 2.7–3.1 ppm(2H), 4.6–5.0 ppm(5H), 5.9–6.1 ppm(2H), 7.1–7.6 ppm(18H), 8.0–8.1 ppm(4H)

$^{13}$CMMR: 36 ppm, 49 ppm, 67 ppm, 68 ppm, 71 ppm, 68 ppm, 71 ppm, 72 ppm, 128–129 ppm, 130.0 ppm, 130.1 ppm, 133 ppm, 134.5 ppm, 135 ppm, 164.7 ppm, 165 ppm, 166 ppm, 169.5 ppm, 170.1 ppm, 170.4 ppm
IR: 3600–2700 cm$^{-1}$, 1800–1650 cm$^{-1}$, 1602 cm$^{-1}$, 1585 cm$^{-1}$, 1529 cm$^{-1}$, 1529 cm$^{-1}$, 1498 cm$^{-1}$, 1453 cm$^{-1}$, 1390 cm$^{-1}$, 1300–1150 cm$^{-1}$, 1140–1030 cm$^{-1}$, 1025 cm$^{-1}$, 907 cm$^{-1}$, 847 cm$^{-1}$, 752 cm$^{-1}$, 714 cm$^{-1}$,

EXAMPLE 16

O,O'-diparaanisoyl-D-tartaric anhydride was reacted with dibenzyl D-aspartate paratoluenesulfonate in the same manner as in Example 12 to obtain O,O'-dipara-anisoyl-D-tartaric acid mono-D-(dibenzyloxycarbonyl)ethylamide of the following formula (20).

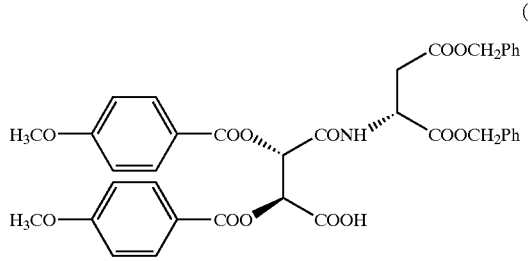

(20)

Its data obtained through analysis are as follows:
m.p.: 52 to 54° C.
$^1$HNMR: 2.8–3.1 ppm(2H), 3.7–3.9 ppm(6H), 40.6–5.0 ppm(5H), 5.9–6.0 ppm(2H), 6.8–8.1 ppm(20H)
$^{13}$CNMR: 36 ppm, 49 ppm, 55 ppm, 67 ppm, 68 ppm, 71 ppm, 72 ppm, 113.6 ppm, 114 ppm, 120 ppm, 121 ppm, 128–129 ppm, 132 ppm, 135 ppm, 164 ppm, 164.5 ppm, 165 ppm, 166 ppm, 170 ppm, 170.5 ppm
IR: 3600–2850 cm$^{-1}$, 2842 cm$^{-1}$, 2584 cm$^{-1}$, 1800–1650 cm$^{-1}$, 1607 cm$^{-1}$, 1581 cm$^{-1}$, 1513 cm$^{-1}$, 1457 cm$^{-1}$, 1443 cm$^{-1}$, 1400 cm$^{-1}$, 1390–1150 cm$^{-1}$, 1094 cm$^{-1}$, 1026 cm$^{-1}$, 970 cm$^{-1}$, 847 cm$^{-1}$, 758 cm$^{-1}$, 697 cm$^{-1}$

EXAMPLE 17

Figure 3:
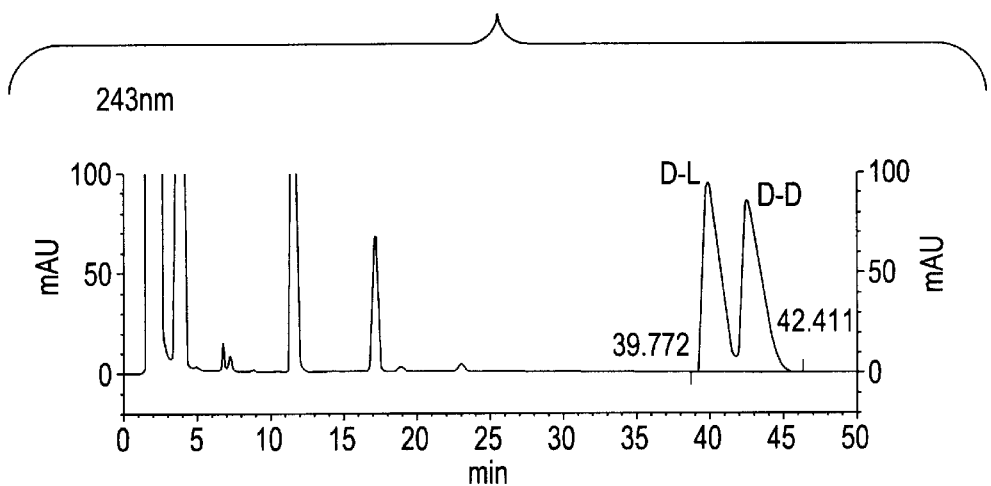
FIG. 3 is a graph showing the HPLC peaks of a mixture of O,O'-diparatoluoyl-D-tartaric acid mono-L-(1-benzyloxycarboyl)ethylamide and O,O'-diparatoluoyl-D-tartaric acid mono-D-(1-benzyloxycarbonyl)ethylamide in Example 17.
Figure 3:
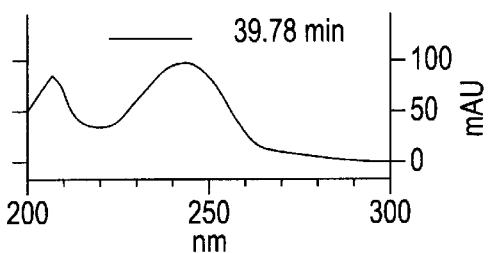
Figure 3:
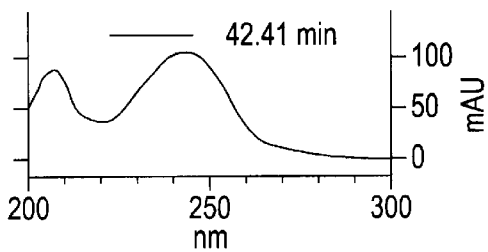

3.5 g (10 mmols) of DL-alanine benzyl ester paratoluenesulfonate was suspended in 50 ml of chloroform, to which was dropwise added 10 ml of aqueous 1 N sodium hydroxide solution with stirring at room temperature. After this was stirred for 30 minutes, the aqueous layer was removed through liquid-liquid separation. 3.5 g (9.5 mmols) of O,O'-diparatoluoyl-D-tartaric anhydride was added to the chloroform layer, and stirred at room temperature for 1 hour. The reaction mixture was analyzed through HPLC, and its chart gave two peaks based on O,O'-diparatoluoyl-D-tartaric acid mono-L-(1-benzyloxycarbonyl)ethylamide (D-L form) of formula (21) and on O,O'-diparatoluoyl-D-tartaric acid mono-D-(1-dibenzyloxycarbonyl)ethylamide (D-D form) of formula (22) (FIG. 3—column, MIGHTYSIL RP-18 GP; eluent aqueous 0.03% ammonia (adjusted to have pH of 4.7 with acetic acid)/acetonitrile=67/33 v/v).

Figure 4:
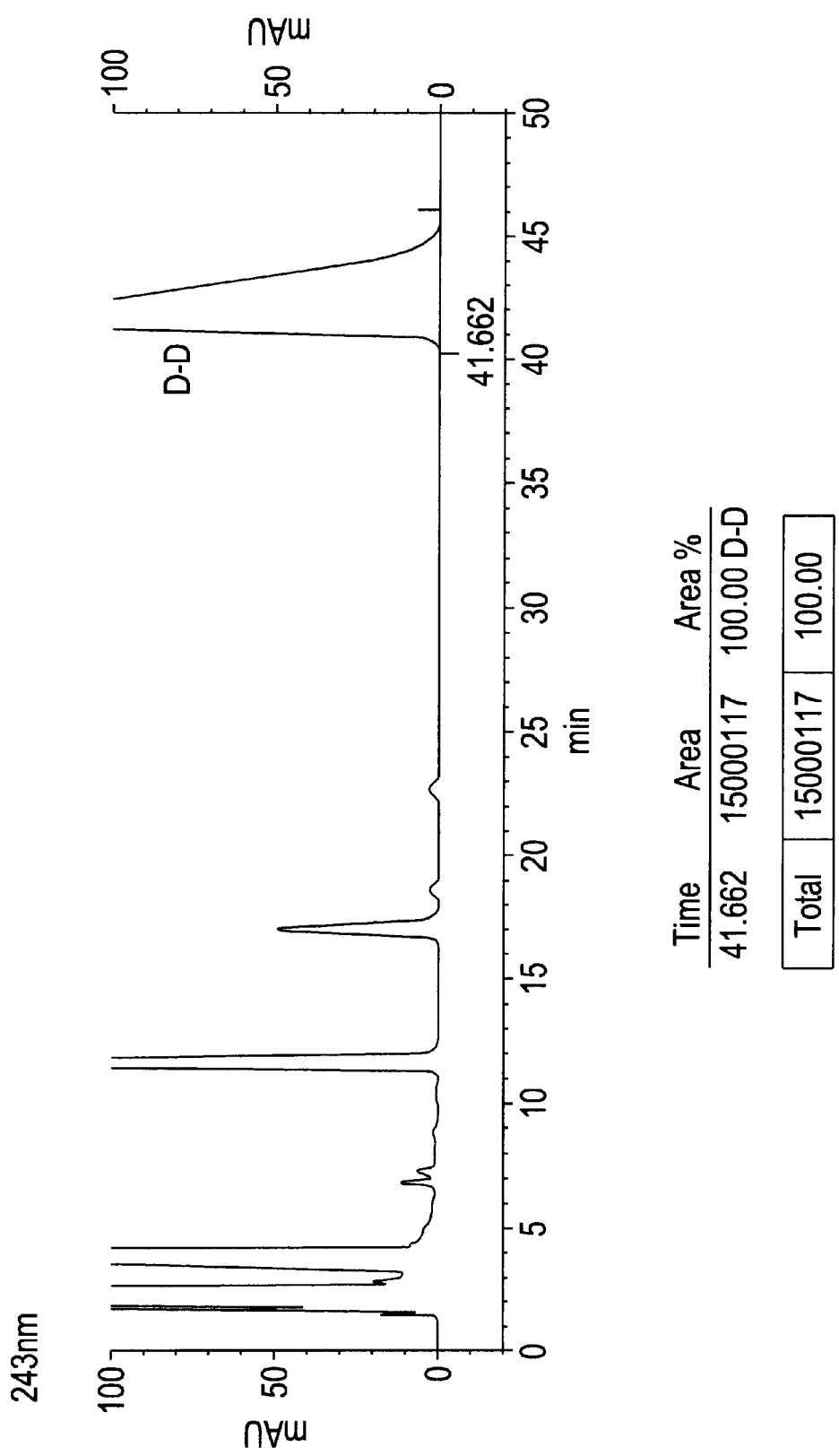
FIG. 4 is a graph showing the HPLC peak of O,O'-diparatoluoyl-D-tartaric acid mono-D-(1-benzyloxycarbonyl)ethylamide in Example 17.

The reaction mixture was concentrated, and the resulting crystals were recrystallized from toluene for optical resolution. The recrystallized crystals were analyzed through HPLC, and its chart gave a single peak for O,O'-diparatoluoyl-D-tartaric acid mono-D-(1-dibenzyloxycarbonyl)ethylamide (D-D form). The optical purity of the thus-resolved product was 99.5% ee or more (FIG. 4—the condition for measurement is the same as that for FIG. 3).

(21)

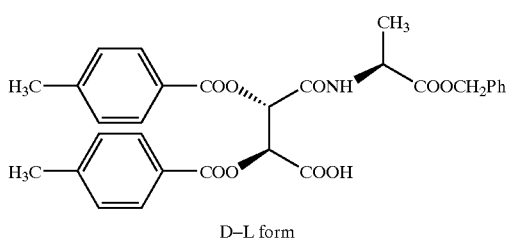

D–L form (22)

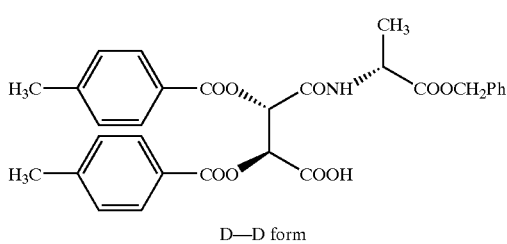

D—D form

EXAMPLE 18

3.2 g (10 mmols) of D-alanine benzyl ester paratoluenesulfonate having an optical purity of 99.6% ee was suspended in 50 ml of chloroform, to which was dropwise added 10 ml of aqueous 1 N sodium hydroxide solution with stirring at room temperature. This was stirred for 30 minutes, and the aqueous layer was removed through liquid-liquid separation. 3.8 g (9.5 mmols) of O,O'-dianisoyl-D-tartaric anhydride (99.9% ee) was added to the chloroform layer, and stirred at room temperature for 1 hour. Next, 15 ml of aqueous 1 N hydrochloric acid was added thereto and stirred for 2 hours, and the aqueous layer was removed through liquid-liquid separation. The chloroform layer was washed with 20 ml of water, then dewatered with anhydrous magnesium sulfate added thereto, and filtered. The filtrate was concentrated, and the crystals thus precipitated were taken out through filtration and dried to obtain O,O'-dianisoyl-D-tartaric acid mono-D-1-benzyloxycarbonylethylamide of formula (23).

(23)

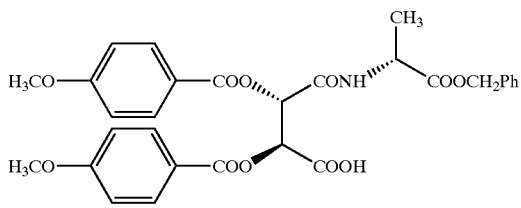

Its data obtained through analysis are as follows:

m.p.: 149 to 152° C.

$^1$HNMR: 1.3–1.5 ppm(3H), 3.7–3.8 ppm(6H), 4.6–4.7 ppm(1H), 5.0–5.2 ppm(2H), 5.8–5.9(1H), 6.0 ppm(1H), 6.8–8.0(20H)

$^{13}$CNMR: 18 ppm, 48 ppm, 55 ppm, 67 ppm, 71 ppm, 72 ppm, 113.6 ppm, 114 ppm, 120 ppm, 121 ppm, 127–132 ppm, 132 ppm, 135 ppm, 163.7 ppm, 164 ppm, 166 ppm, 170 ppm, 172 ppm IR: 3600–2850 cm$^{-1}$, 2842 cm$^{-1}$, 2650 cm$^{-1}$, 1800–1670 cm$^{-1}$, 1663 cm$^{-1}$, 1594 cm$^{-1}$, 1535 cm$^{-1}$, 1508 cm$^{-1}$, 1454 cm$^{-1}$, 1418 cm$^{-1}$, 1390–1200 cm$^{-1}$, 1159 cm$^{-1}$, 1090 cm$^{-1}$, 1022 cm$^{-1}$, 909 cm$^{-1}$, 849 cm$^{-1}$, 760 cm$^{-1}$, 697 cm$^{-1}$

INDUSTRIAL APPLICABILITY

According to the present invention, amino acid dibenzyl esters of high optical purity can be produced through simple operations. In addition, amino acid ester tartramic acids of high optical purity favorable for industrial use can also be produced, not lowering the optical purity of the starting materials used. When starting from racemic amino acid esters, the amino acid ester tartramic acids obtained can be optically resolved through simple operations to give optically-active amino acid ester tartramic acid of high optical purity. In addition, since the reaction of the invention is not accompanied by optical purity reduction, the optical purity of the starting amino acid esters can be obtained with accuracy by analyzing the reaction mixture through ordinary columns.

The compounds are useful for materials for medicines and agricultural chemicals.

What is claimed is:

1. A process for producing optically-active amino acid benzyl esters which comprises reacting an optically-active neutral amino acid or an optically-active basic amino acid of a formula (1):

(1)

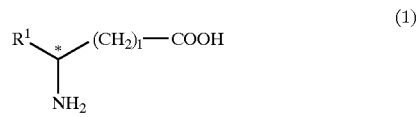

wherein R$^1$ represents a lower alkyl group, an alkoxyalkyl group, a hydroxyalkyl group, a cycloalkyl group, an aminoalkyl group, a carbamoylalkyl group, an aryl group, an arylalkyl group, or an indolylmethyl group; 1 means an integer of from 0 to 2; and * indicates that the compound is optically active, or an optically-active acidic amino acid of a formula (2):

(2)

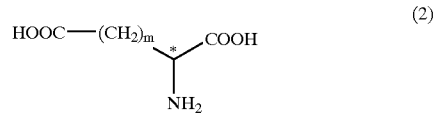

wherein m means an integer of from 1 to 4; and * has the same meaning as above, with a benzyl alcohol of a formula (3):

(3)

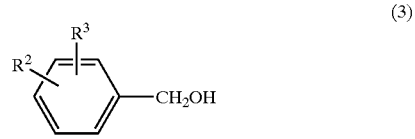

wherein R$^2$ and R$^3$ each represents a hydrogen atom, a lower alkyl group, a lower alkoxyl group, or a halogen atom, and they may be the same or different, in the presence of an acid catalyst to produce an optically-active amino acid benzyl ester of a formula

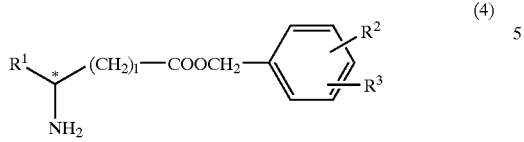
(4)

wherein $R^1$, $R^2$, $R^3$, l and * have the same meaning as above, or an optically-active α-amino acid-dibenzyl ester of a formula (5):

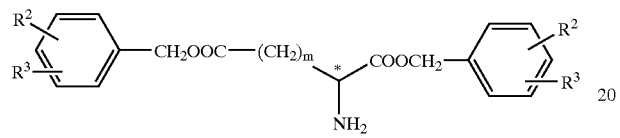
(5)

wherein $R^2$, $R^3$, * and m have the same meaning as above; and which is characterized in that a hydrazine is present in the reaction system.

2. The process for producing optically-active amino acid benzyl esters as claimed in claim 1, wherein the hydrazine is an aromatic hydrazine.

3. The process for producing optically-active amino acid benzyl esters as claimed in claim 2, wherein the aromatic hydrazine to be present in the raction system is represented by a formula (6):

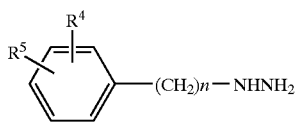
(6)

wherein $R^4$ and $R^5$ each represents a hydrogen atom, a lower alkyl group, a halogen atom, or a nitro group, and they may be the same or different; and n means an integer of from 0 to 3.

4. The process for producing optically-active amino acid benzyl esters as claimed in any one of claims 1 to 3, wherein the compounds are reacted in the absence of oxygen.

5. A process for producing optically-active amino acid benzyl esters, which comprises reacting an optically-active neutral amino acid or an optically-active basic amino acid of a formula (1):

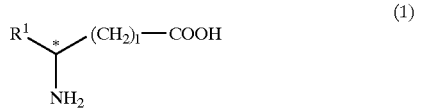
(1)

wherein $R^1$ represents a lower alkyl group, an alkoxyalkyl group, a hydroxyalkyl group, a cycloalkyl group, an aminoalkyl group, a carbomoylalkyl group, an aryl group, an arylalkyl group, or an indolylmethyl group; l means an integer of from 0 to 2; and * indicates that the compound is optically active, or an optically-active acidic amino acid of a formula (2):

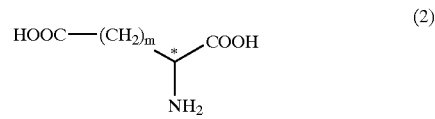
(2)

wherein m means an integer of from 1 to 4; and * has the same meaning as above, with a benzyl alcohol of a formula (3):

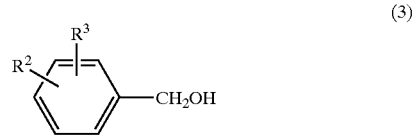
(3)

wherein $R^2$ and $R^3$ each represents a hydrogen atom, a lower alkyl group, a lower alkoxyl group, or a halogen atom, and they may be the same or different, in the presence of an acid catalyst to produce an optically-active amino acid benzyl ester of a formula (4):

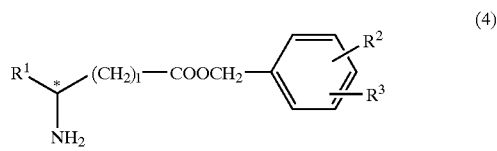
(4)

wherein $R^1$, $R^2$, $R^3$, l and * have the same meaning as above, or an optically-active amino acid dibenzyl ester of a formula (5):

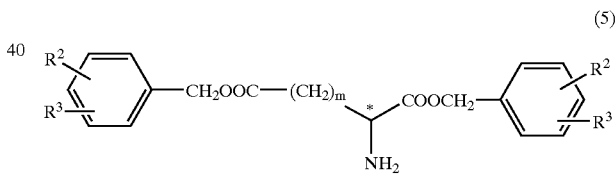
(5)

wherein $R^2$, $R^3$ and m have the same meaning as above;

and which is characterized in that the compounds are reacted in the absence of oxygen.

6. The process for producing optically-active amino acid benzyl esters as claimed in claim 4 or 5, wherein the oxygen concentration in the vapor phase of the reaction systemis at most 3,000 ppm.

7. A process for purifying amino acid benzyl ester sulfonate salts containing impurities comprising:

suspending an amino acid benzyl ester sulfonate salt of a formula

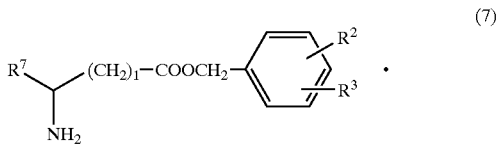
(7)

-continued

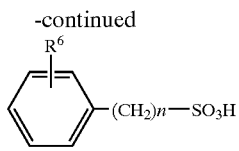

wherein $R^7$ represents a lower alkyl group, an alkoxyalkyl group, a hydroxyalkyl group, a cycloalkyl group, a carbamoylalkyl group, an aryl group, or an arylalkyl group; $R^2$, and $R^3$ each represent a hydrogen atom, a lower alkyl group, a lower alkoxyl group, or a halogen atom, and they may be the same of different, and l is an integer of from 0 to 2; $R^6$ represents a hydrogen atom, or a lower alkyl group having from 1 to 3 carbon atoms, and it is positioned in any of ortho-, meta- or para-position; n falls between 0 and 3; and * indicates that the compound is optically active, or an amino acid dibenzyl ester sulfonate salt of a formula (8):

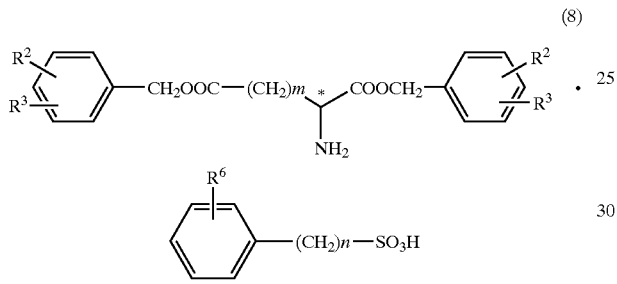

(8)

wherein
$R^2$, $R^3$, $R^6$, and n have the same meanings as above and m is an integer between 1 and 4;
in an organic solvent;
adding water in an amount of at least 2 molar times the amount of the ester or diester sulfonate;
precipitating purified crystals of the ester or diester sulfonate salt; and
filtering out and drying the purified crystals.

8. The process as claimed in claim 7, wherein the organic solvent is at least one selected from the group consisting of aromatic hydrocarbons, aliphatic hydrocarbons, ethers, halides, nitriles and ketones.

9. The process as claimed in claim 7 or 8, wherein the amino acid dibenzyl ester sulfonate salt is an optically-active dibenzyl asparatate sulfonate salt.

10. A process for producing optically-active amino acid benzyl ester tartramic acids of a formula (9) or (10):

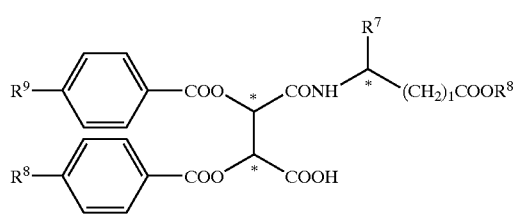

(9)

wherein $R^7$ represents a lower alkyl group, an alkoxyalkyl group, a hydroxyalkyl group, a cycloalkyl group, a carbamoylalkyl group, an aryl group, or an arylalkyl group, $R^8$ represents a lower alkyl group, or a benzyl group, $R^9$ represents a hydrogen atom, a methyl group, or a methoxy group, l is an integer from 0 to 2 and * indicates that the compound is optically active,

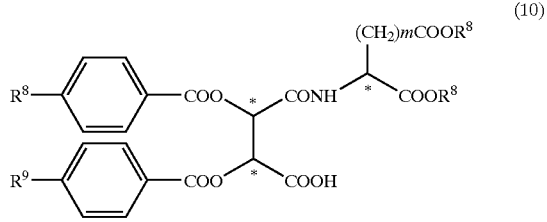

(10)

where m is an integer from 1 to 4 and $R^8$, $R^9$ and * have the same meanings as set forth above in this claim, which comprises reacting an optically-active amino acid ester of a formula (11):

(11)

wherein $R^7$, $R^8$, l and * have the same meanings as set forth above in this claim, or an optically-active amino acid diester of a formula (12):

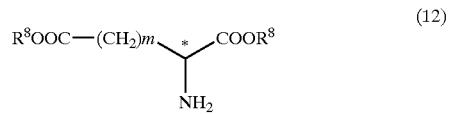

(12)

wherein $R^8$, m and * have the same meanings as set forth above in this claim, with an optically-active diacyltartaric anhydride of a formula (13):

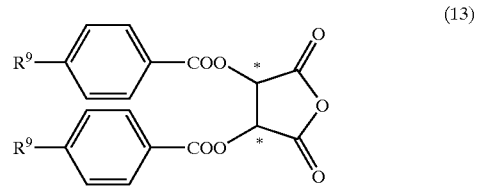

(13)

wherein $R^9$ and * have the same meanings as set forth above in this claim.

11. A process for producing optically-active amino acid ester tartramic acids of a formula (9) or (10):

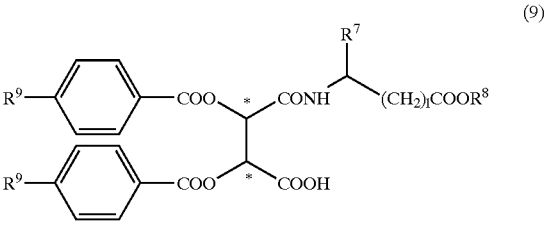

(9)

wherein $R^7$ represents a lower alkyl group, an alkoxyalkyl group, a hydroxyalkyl group, a cycloalkyl group, a carbamoylalkyl group, an aryl group, or an arylalkyl group, $R^8$ represents a lower alkyl group, or a benzyl group, $R^9$ represents a hydrogen atom, a methyl group, or a methoxy group, 1 is an integer from 0 to 2 and * indicates that the compound is optically active,

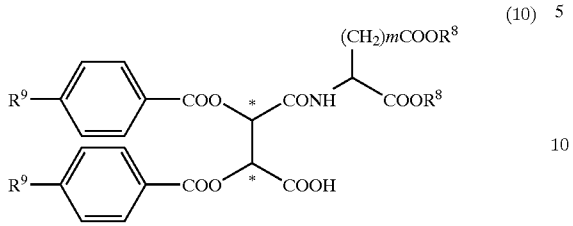

where m is an integer from 1 to 4 and $R^8$, $R^9$ and * have the same meanings as set forth above in this claim, which comprises reacting an amino acid ester of a formula (14):

wherein $R^7$, $R^8$ and 1 have the same meanings as set forth above in this claim, or an amino acid diester of a formula (15):

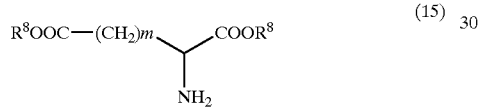

wherein $R^8$ and m have the same meanings as set forth above in this claim, with an optically-active diacyltartaric acid anhydride of a formula (13):

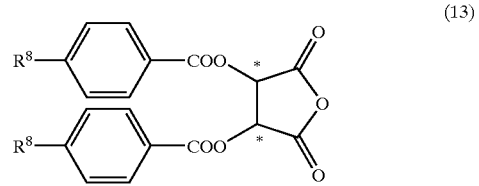

wherein $R^9$ and * have the same meanings as set forth above in this claim, and then optically resolving the resulting product.

12. The process for producing optically-active amino acid ester tartramic acids or optically-active amino acid diester tartramic acids as claimed in claim 10 or 11, wherein the amino acid ester formula (11) is an alanine ester and the amino acid diester of formula (12) is a aspartic acid diester.

13. Optically-active amino acid diester tartramic acids of a formula (10):

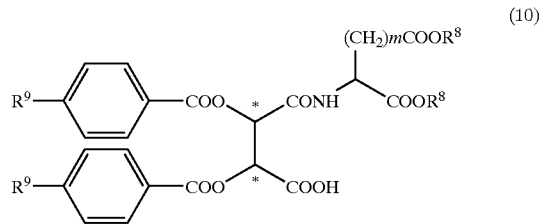

wherein m is an integer from 1 to 4, $R^8$ represents a lower alkyl group, or a benzyl group, $R^9$ represents a hydrogen atom, a methyl group, or a methoxy group, which are optically-active alanine ester tartramic acids and * indicates that the compound is optically active, which are diaspartate tartramic acids.

* * * * *

UNITED STATES PATENT AND TRADEMARK OFFICE
CERTIFICATE OF CORRECTION

PATENT NO. : 6,706,916 B1
DATED : March 16, 2004
INVENTOR(S) : Sato et al.

It is certified that error appears in the above-identified patent and that said Letters Patent is hereby corrected as shown below:

Column 18,
Line 1, please change "–CMMR" to -- $^{13}$CNMR --.

Signed and Sealed this

Twenty-fifth Day of January, 2005

JON W. DUDAS
*Director of the United States Patent and Trademark Office*